(12) United States Patent
Canós et al.

(10) Patent No.: US 8,633,338 B2
(45) Date of Patent: Jan. 21, 2014

(54) PRODUCTION OF MYRTANAL FROM BETA-PINENE EPOXIDE

(75) Inventors: Avelino Corma Canós, Valencia (ES); Michael Renz, Valencia (ES); Olalla De La Torre Alfaro, Valencia (ES)

(73) Assignees: Consejo Superior de Investigaciones Científicas (CSIC), Madrid (ES); Universidad Politécnica de Valencia (UPV), Valencia (ES)

( * ) Notice: Subject to any disclaimer, the term of this patent is extended or adjusted under 35 U.S.C. 154(b) by 0 days.

(21) Appl. No.: 13/517,403

(22) PCT Filed: Dec. 17, 2010

(86) PCT No.: PCT/ES2010/070844
§ 371 (c)(1),
(2), (4) Date: Aug. 24, 2012

(87) PCT Pub. No.: WO2011/086208
PCT Pub. Date: Jul. 21, 2011

(65) Prior Publication Data
US 2012/0330065 A1  Dec. 27, 2012

(30) Foreign Application Priority Data
Dec. 23, 2009  (ES) .................................. 200931260

(51) Int. Cl.
*C07C 45/58* (2006.01)

(52) U.S. Cl.
USPC ....................................................... 568/445

(58) Field of Classification Search
USPC ....................................................... 568/445
See application file for complete search history.

(56) References Cited

PUBLICATIONS

Corma et al. Transformation of Biomass Products into Fine Chemicals Catalyzed by Solid Lewis- and- Bronsted-acids. Topics in Catalysis, 2009, vol. 52, 1182-1189.*

* cited by examiner

*Primary Examiner* — Sikarl Witherspoon
(74) *Attorney, Agent, or Firm* — Blank Rome LLP

(57) ABSTRACT

The present invention refers to a process for the production of myrtanal from β-pinene epoxide that comprises at least of putting this epoxide in contact with a microporous and crystalline catalyst with pores of a diameter of at least 0.52 nm with an empirical formula for the calcinated and dehydrated form of $$H_w(M_w Ti_x Sn_y Zr_z Si_{1-w-x-y-z})O_2$$

where
M is at least a metal with valence+3 selected from Al, B, Ga, Fe, Cr and combinations of these;
w is a molar fraction of M with a value of between 0 and 2(x+y+z);
x is a molar fraction of titanium and has a value of between 0 and 0.06;
y is a molar fraction of tin and has a value of between 0 and 0.06;
z is a molar fraction of zirconium and has a value of between 0 and 0.06;
and where at least one of the three values "x", "y" or "z" is different from zero.
In the present invention, the microporous and crystalline catalyst preferably has pores of at least 0.52 nm and has a crystalline structure with an X-ray diffractogram of a zeolite beta.

13 Claims, 2 Drawing Sheets

PRODUCTION OF MYRTANAL FROM BETA-PINENE EPOXIDE

This application is the U.S. national phase of International Patent Application No. PCT/ES2010/070844, filed Dec. 17, 2010, which claims the benefit of Spanish Patent Application No. P200931260, filed Dec. 23, 2009.

FIELD OF THE INVENTION

The present invention belongs to the field of processes for conversion of epoxides by transposition using a solid catalyst.

STATE OF PRIOR ART

Myrtanal is a natural monoterpene that is found in various plants. For example, 25% myrtanal has been found in the roots of *Guem urbanum* (Deut. Apotheker Zeit. 1995, 135, 32-44), a plant used in medicine since antiquity. Myrtanal has been found in the roots of Greek Paeonia, which has antimicrobial activity and has been used since antiquity to clean wounds. Traces have also been found in "Iranian damask rose" oil (Anal. Chim. Acta 2008, 623, 11-21). Until recently, no process has been found to isolate myrtanal directly from biomass.

However, myrtanal can be obtained by transposition of β-pinene epoxide. β-pinene epoxide is easily accessible by epoxidation and the substrate of epoxidation, β-pinene, is obtained economically from biomass as it forms part of the white spirit from pine resin and can be separated by simple distillation (H. Suburg, J. Panten, Common Fragrance and Flavor Materials, Wiley-VCH, 5$^{th}$ edition, Weinheim, 2006). The epoxidation reaction of β-pinene is well documented in the literature. For example, the corresponding epoxide can be obtained with oxygenated water in the presence of a catalyst (J. Catal. 2008, 256, 154-158) or with organic peracids such as for example meta-chloroperbenzoic acid (Synth. Comm. 2007, 37, 3529-3539). Such peracids can be formed in situ from an aldehyde and oxygen (Catal. Lett. 2007, 113, 155-159). These references are only some examples of a long list of epoxidations of β-pinene that can be found in the literature, without counting the methods of selective epoxidation that have not been applied to the substrate and that give good results with high probability. In conclusion, β-pinene epoxide can be easily obtained and at an economic price for the production of organic compounds to be used by the fine chemicals industry.

β-pinene epoxide is a strained molecule due to its bicyclic structure in addition to the three atom epoxide ring. The tension in the molecule can be released in various ways by a transposition and myrtanal is not the only product that can result. Other possible products of the transposition are myrtenol and perillyl alcohol. From the latter, secondary products can be obtained by isomerisation of its double bonds. These alternative products of the transposition hinder the development of an economic process, as the catalyst has to be very selective in order to avoid unwanted products.

Transpositions of β-pinene epoxide to myrtanal can be divided into two groups; those taking place in the presence of a soluble catalyst and those taking place in the presence of an insoluble catalyst. As a soluble catalyst, para-toluenesulfonic acid is used, obtaining a mixture of products with a myrtanal content of 17% (J. Chem. Soc. Perkin Trans. 1994, 1419-1422). A process for a cascade reaction has been described, including the epoxidation of β-pinene and the transposition of the corresponding epoxide in the presence of a manganese catalyst to give myrtanal with a maximum yield of 30% and a selectivity of 54% (Catal. Lett. 1996, 42, 213-215).

Already in 1959, Kergomard and Philibert obtained myrtanal from β-pinene epoxide with a yield of 44% simply by refluxing in the presence of alumina (Bull. Soc. Chim. Fr. 1959, 1381-1385). If the alumina is modified with sodium hydroxide, the selectivity towards myrtanal falls to only 6% (Tetrahedron 1977, 33, 2955-1957). The modification of alumina with rare earths such as $Y_2O_3$ and $Eu_2O_3$ gives, in the majority of cases, a selectivity of around 50% (Bull. Chem. Soc. Jpn. 1995, 68, 89-94). A considerable improvement is achieved by using a material such as tin incorporated in an amorphous silicate with a mesoporous structure with 35 Å channels as a catalyst (Top. Catal. 2009, 52, 1182-1189). Thus selectivity for myrtanal was 82% at complete conversion in the first catalytic cycle and fell to 76% at complete conversion in the fourth reuse. If silicate analogues with other metals such as titanium and zirconium are used, selectivity for myrtanal falls to 49% and 35% respectively. In addition, in the case of zirconium, conversion was only 45%.

In summary, until the present day, the best catalyst for the conversion of β-pinene epoxide to myrtanal is a silicate with amorphous tin arranged to that it can be recycled various times with a small decrease of selectivity.

DESCRIPTION OF THE INVENTION

The present invention refers to a process for the production of myrtanal from β-pinene epoxide that comprises at least of putting this epoxide in contact with a microporous and crystalline catalyst with pores of a diameter at least 0.52 nm with an empirical formula for the calcinated and dehydrated form of

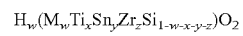

$$H_w(M_wTi_xSn_yZr_zSi_{1-w-x-y-z})O_2$$

where

M is at least a metal with valence+3 selected from Al, B, Ga, Fe, Cr and combinations of these;

w is a molar fraction of M and has a value of between 0 and 2(x+y+z);

x is a molar fraction of titanium and has a value of between 0 and 0.06;

y is a molar fraction of tin and has a value of between 0 and 0.06;

z is a molar fraction of zirconium and has a value of between 0 and 0.06;

and where at least one of the three values "x", "y" or "z" is different from zero.

The present invention guarantees obtaining the product myrtanal with high selectivity, which has not been achieved up till now with other solid or soluble catalysts. It should be pointed out that other catalysts with the same empirical formula but with an amorphous structure do not provide such a high level of selectivity as described in the present invention, neither do crystalline materials with other empirical formulae.

Preferably, the microporous and crystalline catalyst has pores of at least 0.52 nm and has a crystalline structure with an X-ray diffractogram of a zeolite beta.

According to a particular embodiment, in the formula for the catalyst in the calcinated and dehydrated form, "x" has a value of between 0.002 and 0.06, "y" has a value of between 0 and 0.06 and "z" has a value of between 0 and 0.06.

According to another particular embodiment, in the formula for the catalyst in the calcinated and dehydrated form, "y" has a value of between 0.002 and 0.06, "x" has a value of between 0 and 0.06 and "z" has a value of between 0 and 0.06.

According to a particular embodiment, in the formula for the catalyst in the calcinated and dehydrated form, "z" has a value of between 0.002 and 0.006, "x" has a value of between 0 and 0.06 and "y" has a value of between 0 and 0.06.

According to another particular embodiment, the transposition of β-pinene epoxide to myrtanal is characterised in that it is carried out in the presence of a solvent.

In addition, according to the present invention, the solvent can be selected from the group of acetonitrile, dioxane, nitromethane, diethyl ether, methyl tert-butyl ether, toluene, methanol, ethanol, isopropanol and mixtures of these. Preferably, the solvent is acetonitrile.

According to another particular embodiment, the epoxide is in a solution of 10% to 90% by weight, more preferably, from 10% to 50% by weight.

In addition, the transposition of β-pinene epoxide to myrtanal is preferably carried out at a temperature of between 20° C. and 150° C., more preferably between 40° C. and 120° C. and over a period of contact that can be between 5 minutes and 24 hours, and more preferably between 10 minutes and 15 hours.

Also, the process can be carried out in a discontinuous or in a continuous reactor. In continuous mode, the catalyst can be used in a fixed bed, ebullient bed, mobile bed or in any other known configuration.

The crystalline and microporous catalysts that can be used in accordance with the present invention can be prepared by a process of hydrothermal crystallisation in which a reaction mixture is prepared by combining sources of zirconium, tin, titanium, silicon, an organic structure-directing agent, optionally a metal with valence+3 and water. The sources of silicon include, although without limitation, colloidal silica, amorphous silica, pyrogenic silica, silica gel and tetraalkyl orthosilicate. The sources of aluminum may include, although without limitation, aluminum halides, aluminum alkoxides, aluminum oxides, metallic aluminum, alkaline metal aluminates, alkaline earth metal aluminates and other salts of aluminum. Sources of zirconium include zirconium halides, zirconyl halides, zirconium alkoxides, zirconium oxides, metallic zirconium, alkaline metal zirconates, alkaline earth metal zirconates and organometallic compounds of zirconium, without these examples being limiting.

A preferred source is zirconium tetrachloride or zirconyl chloride. Examples of zirconium alkoxides include zirconium butoxide, zirconium ethoxide and zirconium propoxide. Sources of tin include tin halides, tin alkoxides, tin oxides, metallic tin, alkaline metal stannates, alkaline earth metal stannates and tin organometallic compounds, without these examples being limiting. A preferred source is tin tetrachloride. Examples of tin alkoxides include tin butoxide, tin ethoxide and tin propoxide.

Sources of titanium include titanium halides, titanium alkoxides, titanium oxides, metallic titanium, alkaline metal titanates, alkaline earth titanates and titanium organometallic compounds, without these examples being limiting. A preferred source is titanium tetraisopropoxide. Examples of titanium alkoxides include titanium butoxide, titanium ethoxide and titanium propoxide. Organic structure-directing agents include tetraalkylammonium ions such as a tetraethylammonium ion, aza-polycyclic compounds such as 1,4-diazabicyclo[2.2.2]octane, dialkyl-dibenzylammoniun ions such as a dimethyl-dibenzylammonium ion and bis-piperidinyl ions such as a 4,4'-trimethylene-bis-(N-benzyl-N-methyl piperidine) ion, without these being limiting. These ions can be used as hydroxides or halides.

As mobilising agents of the precursor species, the hydroxyl or fluoride ions are used. Synthesis is carried out in a hydrothermal system at temperatures between 120° C. and 195° C. for periods of between 12 hours and 40 days.

Once the material has crystallised, the solids are separated from the liquids by filtration or centrifugation and washed with water until a pH of around 9 is reached. Finally the dry solid is calcinated in air or $N_2$ followed by air at temperatures between 400° C. and 1000° C. in order to remove occluded organic molecules from the interior of the pores.

The preferred molecular sieve structure in the present invention corresponds to that of zeolite beta and to its possible individual polymorphs or their combinations. In the case of zeolite beta, the X-ray diffractogram shows at least the peaks and intensities presented in Table A. The intensities presented in Table A are the relative intensities that are obtained relating the intensity of each peak (I) to that of the strongest line ($I_0$). The intensity is calculated by the equation $100 \times I/I_0$ and is represented by mf, f, m and d where these are defined as: f=80-100, m=20-80 and d=0-20.

TABLE A

| 2 Θ | d (Å) | Relative intensity |
|---|---|---|
| 7.22 | 12.23 | m |
| 7.76 | 11.38 | m |
| 21.54 | 4.12 | d |
| 22.57 | 3.94 | f |
| 22.96 | 3.87 | d |
| 25.45 | 3.50 | d |
| 27.00 | 3.30 | d |
| 29.00 | 3.08 | d |
| 29.65 | 3.01 | d |
| 30.60 | 2.92 | d |

Therefore, according to a preferred embodiment, the catalyst has pores with a diameter of at least 0.52 nm and with a crystalline structure with an X-ray diffractogram of a zeolite beta.

The synthesised zeolite is activated for catalytic reactions, generally by calcination at a temperature between 300° C. and 1000° C. for a time generally between 1 and 20 hours. As mentioned before, the crystalline and microporous catalysts described above have a very good activity and a very high selectivity as catalysts for obtaining myrtanal from β-pinene epoxide.

Throughout the description and the claims, the use of the word "comprise" and its variants is not intended to exclude other technical characteristics, additives, components or steps. For experts in the subject, other purposes, advantages and characteristics of the invention will follow in part from the description and in part from the practice of the invention. The following examples and figures are provided for illustration purposes and are not intended to limit the scope of the present invention.

EXAMPLES OF THE INVENTION

The following examples are intended to illustrate features related to the invention.

EXAMPLES

Example 1

Preparation of Zeolite Beta Seeds Used to Obtain Zeolite Beta with Metals

In a reactor, 1.85 grams of $AlCl_3 \cdot 6H_2O$ were dissolved in 4.33 grams water. To this solution, 45.2 grams of tetraethylammonium hydroxide (TEAOH) (35% by weight aqueous solution) were added. Next, 40 grams of tetraethyl orthosilicate (TEOS) were added and the mixture stirred until the ethanol formed by the hydrolysis of TEOS had evaporated. The composition of the resulting gel was:

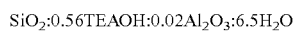
$SiO_2:0.56TEAOH:0.02Al_2O_3:6.5H_2O$

The solution obtained was transferred to a stainless steel autoclave with interior walls protected by Teflon®, heated to 140° C. and left to react for 3 days with stirring. The product was recovered by centrifugation, washed with distilled water and dried at 100° C. The product showed the structure of a zeolite beta with a crystallinity greater than 90%.

The sample of the zeolite beta of the previous paragraph was dealuminated by treating 1 gram of the zeolite with 60 grams of HNO3 (60% by weight) at 80° C. for 24 hours. The solid was recovered by filtration, washed with distilled water and dried at 100° C. The crystallinity of this product was 70% and the ratio of Si/Al was determined by elemental analysis and was greater than 2000.

Example 2

Synthesis of a Zirconium Silicate with the Structure of a Zeolite Beta

In a reactor, 30 grams TEOS and 33.0 grams of TEAOH (35% by weight) were mixed. Next, a solution of 0.39 grams $ZrOCl_2 \cdot 8H_2O$ (98%) in 2.75 grams water was added and the mixture stirred until the ethanol formed by the hydrolysis of the TEOS had evaporated. To the solution obtained, 3.27 grams of hydrofluoric acid (48% by weight) was added and a viscous paste was obtained. Finally, a suspension of 0.36 grams dealuminated seeds of zeolite beta prepared according to Example 1 was added in 2 grams water. The final composition of the gel is represented by the formula:

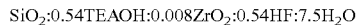
$SiO_2:0.54TEAOH:0.008ZrO_2:0.54HF:7.5H_2O$

Figure 1:
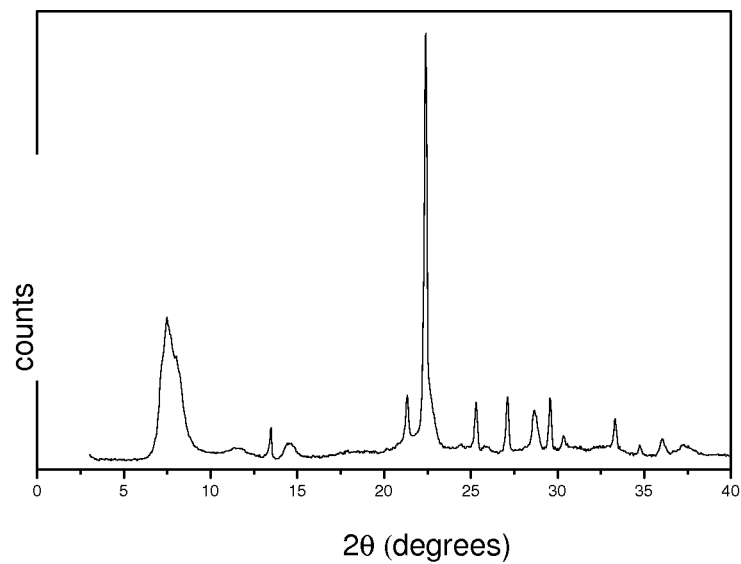
FIG. 1. X-ray powder diffraction pattern of sample A.

The paste obtained was transferred to a stainless steel autoclave with interior walls protected by Teflon®, heated to 140° C. and left to react for 14 days with stirring. After this time, the product was recovered by filtration. The product was demonstrated to have the structure of a zeolite beta with a crystallinity close to 100% by X-ray diffraction. FIG. 1 shows an example of an X-ray powder diffraction pattern of the calcinated crystalline structure. Elemental analysis of the two samples gave a ratio of silicon/zirconium of 130 and 116. The product was calcinated at 580° C. for 3 hours and maintained its crystallinity. These products were labelled sample A (rel. 130) and sample B (rel. 116). (See FIG. 1).

Example 3

Synthesis of a Tin Silicate with the Structure of a Zeolite Beta

In a reactor, 30 grams TEOS and 33.0 grams of TEAOH (35% by weight) were mixed. Next, a solution of 0.43 grams $SnCl_4 \cdot 5H_2O$ (98%) in 2.75 grams water was added and the mixture stirred until the ethanol formed by the hydrolysis of the TEOS had evaporated. To the solution obtained, 3.27 grams of hydrofluoric acid (48% by weight) was added and a viscous paste was obtained. Finally, a suspension of 0.36 grams dealuminated seeds of zeolite beta prepared according to Example 1 was added in 2 grams water. The final composition of the gel is represented by the formula:

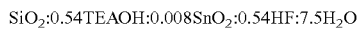
$SiO_2:0.54TEAOH:0.008SnO_2:0.54HF:7.5H_2O$

The paste obtained was transferred to a stainless steel autoclave with interior walls protected by Teflon®, heated to 140° C. and left to react for 18 days with stirring. After this time, the product was recovered by filtration. The product was demonstrated to have the structure of a zeolite beta with a crystallinity close to 95% by X-ray diffraction. Elemental analysis gave a ratio of silicon/tin of 130. The product was calcinated at 580° C. for 3 hours and maintained its crystallinity. This product was labelled sample C.

Example 4

Synthesis of a Titanium Silicate with the Structure of a Zeolite Beta

In a reactor, 30 grams TEOS and 0.66 grams of $Ti(OEt)_4$ (99% by weight) were mixed. Next, a solution of 33.0 grams TEAOH (35% by weight) in 3 grams water was added and the mixture stirred until the ethanol formed by the hydrolysis of the TEOS had evaporated. To the solution obtained, 3.27 grams of hydrofluoric acid (48% by weight) was added and a viscous paste was obtained. Finally, a suspension of 0.36 grams dealuminated seeds of zeolite beta prepared according to Example 1 was added in 2 grams water. The final composition of the gel is represented by the formula:

$SiO_2:0.54TEAOH:0.02TiO_2:0.54HF:7.5H_2O$

The paste obtained was transferred to a stainless steel autoclave with interior walls protected by Teflon®, heated to 140° C. and left to react for 7 days with stirring. After this time, the product was recovered by filtration. The product was demonstrated to have the structure of a zeolite beta with a crystallinity close to 100% by X-ray diffraction. Elemental analysis gave a ratio of silicon/titanium of 132. The product was calcinated at 580° C. for 3 hours and maintained its crystallinity. This product was labelled sample D.

Example 5

Synthesis of a Zirconium and Tin Silicate with the Structure of a Zeolite Beta In a reactor, 30 grams TEOS and 33.0 grams of TEAOH (35% by weight) were mixed. Next, a solution of 0.19 grams $ZrOCl_2 \cdot 8H_2O$ (98%) in 2.75 grams water and a solution of 0.43 grams $SnCl_4 \cdot 5H_2O$ (98%) in 2.75 grams water was added and the mixture stirred until the ethanol formed by the hydrolysis of the TEOS had evaporated. To the solution obtained, 3.27 grams of hydrofluoric acid (48% by weight) was added and a viscous paste was obtained. Finally, a suspension of 0.36 grams dealuminated seeds of zeolite beta prepared according to Example 1 was added in 2 grams water. The final composition of the gel is represented by the formula:

$SiO_2:0.54TEAOH:0.004ZrO_2:0.008SnO_2:0.54HF:$
$7.5H_2O$

The paste obtained was transferred to a stainless steel autoclave with interior walls protected by Teflon®, heated to 140°

C. and left to react for 30 days with stirring. After this time, the product was recovered by filtration. The product was demonstrated to have the structure of a zeolite beta with a crystallinity close to 90% by X-ray diffraction. Elemental analysis gave a ratio of silicon/zirconium of 249 and a ratio of silicon/tin of 114. The product was calcinated at 580° C. for 3 hours and maintained its crystallinity. This product was labelled sample E.

Example 6

Synthesis of a Zirconium and Tin Silicate with the Structure of a Zeolite Beta

In a reactor, 30 grams TEOS and 33.0 grams of TEAOH (35% by weight) were mixed. Next, a solution of 0.39 grams $ZrOCl_2 \cdot 8H_2O$ (98%) in 2.75 grams water and a solution of 0.43 grams $SnCl_4 \cdot 5H_2O$ (98%) in 2.75 grams water was added and the mixture stirred until the ethanol formed by the hydrolysis of the TEOS had evaporated. To the solution obtained, 3.27 grams of hydrofluoric acid (48% by weight) was added and a viscous paste was obtained. Finally, a suspension of 0.36 grams dealuminated seeds of zeolite beta prepared according to Example 1 was added in 2 grams water. The final composition of the gel is represented by the formula:

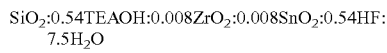
$SiO_2$:0.54TEAOH:0.008$ZrO_2$:0.008$SnO_2$:0.54HF: 7.5$H_2O$

The paste obtained was transferred to a stainless steel autoclave with interior walls protected by Teflon®, heated to 140° C. and left to react for 30 days with stirring. After this time, the product was recovered by filtration. The product was demonstrated to have the structure of a zeolite beta with a crystallinity close to 95% by X-ray diffraction. Elemental analysis gave a ratio of silicon/zirconium of 198 and a ratio of silicon/tin of 96. The product was calcinated at 580° C. for 3 hours and maintained its crystallinity. This product was labelled sample F.

Example 7

Synthesis of a Titanium and Zirconium Silicate with the Structure of a Zeolite Beta In a reactor, 30 grams TEOS and 0.55 grams of $Ti(OEt)_4$ (99% by weight) were mixed. Next, a solution of 33.0 grams TEAOH (35% by weight) in 3 grams water and a solution of 0.39 grams $ZrOCl_2 \cdot 8H_2O$ (98%) in 2.75 grams water was added and the mixture stirred until the ethanol formed by the hydrolysis of the TEOS had evaporated. To the solution obtained, 3.27 grams of hydrofluoric acid (48% by weight) was added and a viscous paste was obtained. Finally, a suspension of 0.36 grams dealuminated seeds of zeolite beta prepared according to Example 1 was added in 2 grams water. The final composition of the gel is represented by the formula:

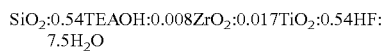
$SiO_2$:0.54TEAOH:0.008$ZrO_2$:0.017$TiO_2$:0.54HF: 7.5$H_2O$

The paste obtained was transferred to a stainless steel autoclave with interior walls protected by Teflon®, heated to 140° C. and left to react for 30 days with stirring. After this time, the product was recovered by filtration. The product was demonstrated to have the structure of a zeolite beta with a crystallinity close to 100% by X-ray diffraction. Elemental analysis gave a ratio of silicon/zirconium of 127 and a ratio of silicon/titanium of 144. The product was calcinated at 580° C. for 3 hours and maintained its crystallinity. This product was labelled sample G.

Example 8

Synthesis of a Silicate with the Structure of a Zeolite Beta

In a reactor, 30 grams TEOS and 33.0 grams of TEAOH (35% by weight) were mixed. Next, the mixture was stirred until the ethanol formed by the hydrolysis of TEOS had evaporated. To the solution obtained, 3.27 grams of hydrofluoric acid (48% by weight) was added and a viscous paste was obtained. Finally, a suspension of 0.36 grams dealuminated seeds of zeolite beta prepared according to Example 1 was added in 2 grams water. The final composition of the gel is represented by the formula:

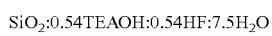
$SiO_2$:0.54TEAOH:0.54HF:7.5$H_2O$

The paste obtained was transferred to a stainless steel autoclave with interior walls protected by Teflon®, heated to 140° C. and left to react for 5 days with stirring. After this time, the product was recovered by filtration. The product was demonstrated to have the structure of a zeolite beta with a crystallinity close to 100% by X-ray diffraction. The product was calcinated at 580° C. for 3 hours and maintained its crystallinity. This product was labelled sample H.

Example 9

Synthesis of a Zirconium Silicate with an Ordered Mesoporous Non-Crystalline Structure To 5.48 g of $C_{16}$TMABr, 36.6 g of Milli-Q water and 9.46 g TMAOH (25% in water) were added. The resulting mixture was heated to 40° C. for a few minutes for the complete solution of the surfactant, 0.32 grams of $ZrOCl_2 \cdot 8H_2O$ were added and the synthesis mixture stirred for 5 min at 250 revolutions per minute with a mechanical stirrer. Lastly, 6 g of Aerosil 200 were added, maintaining the stirring for 1 hour. The final composition of the gel is represented in the formula:

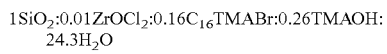
1$SiO_2$:0.01$ZrOCl_2$:0.16$C_{16}$TMABr:0.26TMAOH: 24.3$H_2O$

Figure 2:
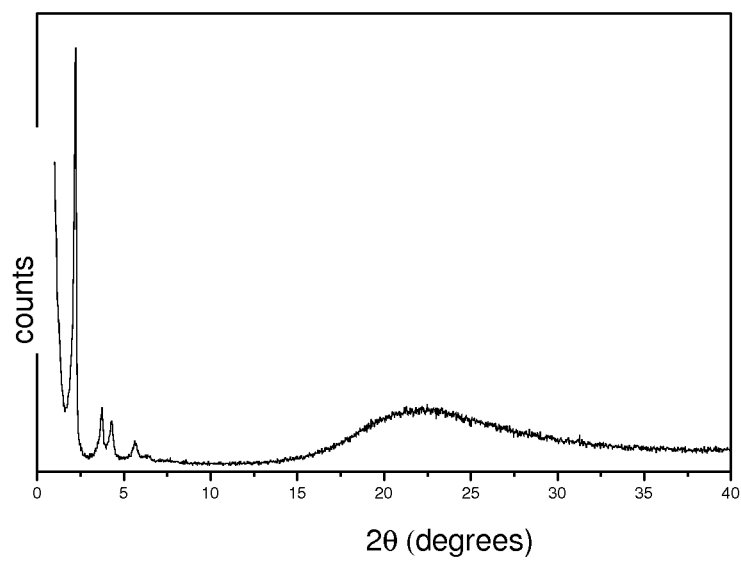
FIG. 2. X-ray powder diffraction pattern of sample I.

The resulting gel was introduced into a stainless steel autoclave with a Teflon® interior sleeve and heated to 135° C. for 24 hours. The solid was recovered by filtration, washed with abundant deionised water and dried at 60° C. overnight. The material obtained presented the structure MCM-41 as shown in FIG. 2. Organic matter was removed by calcination at 540° C. in a flow of nitrogen and in dry air. The calcinated sample had a content of 1% $ZrO_2$, an area (BET) of 1050 $m^2/g$, a pore volume of 0.74 $cm^3/g$ and a pore diameter of 35 Å. This product was labelled sample I (see FIG. 2).

Example 10

Synthesis of a Zirconium Silicate with an Unordered Non-Crystalline Structure

A solution of 2 g tetramethyl orthosilicate (TMOS), 0.021 g of zirconyl chloride ($ZrOCl_2$) and 1.68 g methanol was added to another aqueous solution of 0.0015 g $NH_4F$ dissolved in 0.95 g Milli-Q water. The addition was carried out at room temperature with constant stirring and drop by drop. The mixture was left stirring constantly until the sudden appearance of a thick gel after a few minutes of the addition of the $NH_4F$.

The molar composition of the resulting gel was:

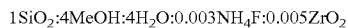
1$SiO_2$:4MeOH:4$H_2O$:0.003$NH_4F$:0.005$ZrO_2$

Figure 3:
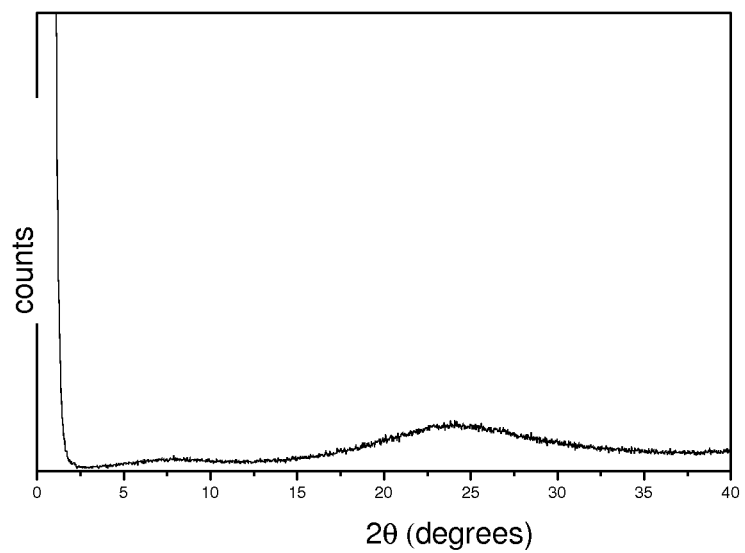
FIG. 3. X-ray powder diffraction pattern of sample J.

Next, the gel formed was allowed to age for 24 hours in a water bath at 36° C. Finally, the gel was dried in an oven at 150° C. for 24 hours, obtaining 0.80 g of solid. Elemental analysis gave the content as 0.7% zirconium by weight. The product was calcinated at 500° C. for 3 hours. This product was labelled sample J and its X-ray powder diffraction pattern is shown in FIG. 3.

Example 11

Use of Catalyst A in the Transposition of β-Pinene Epoxide to Myrtanal 600 mg β-pinene epoxide was dissolved in 3.0 g solvent. 50 mg of material A was added and the mixture was stirred at 80° C. for two hours. The product mixture was analysed by gas chromatography in Varian 3900 GC equipment with a Carbowax column (length 15 m, internal diameter 0.32 mm and particle thickness of 0.25 μm). The results are summarised in Table 1.

Myrtanal was identified by mass spectroscopy coupled to the gas chromatography equipment in the crude product of the reaction and by NMR spectroscopy after concentration by distillation: MS m/z (%): 152(2) [M]$^+$, 29(47), 39(58), 41(100), 67(91), 69(80), 81(70), 82(63), 83(37), 123(54); $^{13}$C NMR (75 MHz, CDCl$_3$) δ=204.0, 49.0, 40.5, 40.2, 39.4, 26.2, 23.9, 23.5, 20.4, 12.9.

TABLE 1

| input | solvent | reaction time [h] | conversion [%] | selectivity for myrtanal [%] |
|---|---|---|---|---|
| 1 | acetonitrile | 2.0 | 98 | 94 |
| 2 | toluene | 1.0 | 97 | 89 |
| 3 | nitromethane | 0.5 | >98 | 87 |
| 4 | 1,4-dioxane | 0.5 | >98 | 90 |

Example 12

Repeated use of Catalyst A in the Transposition of β-Pinene Epoxide to Myrtanal 6.00 g β-pinene epoxide was dissolved in 30 g acetonitrile. 500 mg of material A was added and the mixture was stirred at 80° C. for two hours. The catalyst was recovered by filtration and reactivated by calcination for 3 h at 580° C. In the subsequent use, all the quantities of the reagents were escalated according to the amount of catalyst available. The analysis of the product mixtures was carried out as described in example 11. The results are summarised in Table 2.

TABLE 2

| input | recycling count | conversion [%] | selectivity for myrtanal [%] |
|---|---|---|---|
| 1 |   | 97 | 92 |
| 2 | 1 | >98 | 94 |
| 3 | 2 | >98 | 93 |
| 4 | 3 | 98 | 91 |
| 5 | 4 | >98 | 93 |
| 6 | 5 | >98 | 94 |
| 7 | 6 | >98 | 94 |
| 8 | 7 | >98 | 93 |
| 9 | 8 | >98 | 93 |

Example 13

Use of Catalyst B in the Transposition of β-Pinene Epoxide to Myrtanal in a Fixed Bed Reactor Particles of sizes between 0.4 and 0.6 mm of material B were prepared. 800 mg was placed in a stainless steel tube of 14 cm length and 4 mm internal diameter. The tube was heated and the feed was passed at a velocity of 0.5 mL/min. The feed consisted of β-pinene epoxide with 17% by weight acetonitrile. For reactivation of the catalyst, the feed was stopped and a flow of air (30 mL/min) at 500° C. was passed for 20 min. After cooling to 80° C., the reaction was resumed. The product obtained was analysed as described in example 11. The results are summarised in Table 3.

TABLE 3

| input | reaction time [min] | conversion [%] | selectivity for myrtanal [%] |
|---|---|---|---|
| 1 | 10 | >98 | 91 |
| 2 | 20 | >98 | 92 |
| 3 | 30 | >98 | 89 |
| 4 | 40 | >98 | 91 |
| 5 | 50 | >98 | 92 |
| 6 | 60 | >98 | 92 |
| 7 | 70 | >98 | 91 |
| 8 | 80 | >98 | 92 |
|   | activation |   |   |
| 9 | 10 | >98 | 92 |
| 10 | 20 | >98 | 95 |
| 11 | 30 | >98 | 97 |
| 12 | 40 | >98 | 96 |
| 13 | 50 | >98 | 95 |
| 14 | 60 | >98 | 97 |
| 15 | 70 | >98 | 97 |
| 16 | 80 | >98 | 96 |

Example 14

Use of Catalysts A, C, D, E, F and G in the Transposition of β-Pinene Epoxide to Myrtanal 600 mg β-pinene epoxide was dissolved in 3.0 g acetonitrile. 50 mg of material A, C, D, E, F or G was added and the mixture was stirred at 80° C. for two hours. The analysis of the product mixtures was carried out as described in example 11. The results are summarised in Table 4.

TABLE 4

| input | catalyst | conversion [%] | selectivity for myrtanal [%] |
|---|---|---|---|
| 1 | A | 98 | 94 |
| 2 | C | 98 | 89 |
| 3 | D | 74 | 86 |
| 4 | E | 98 | 95 |
| 5 | F | 98 | 95 |
| 6 | G | 88 | 95 |
| 7 | G$^a$ | 96 | 96 |

$^a$after a reaction time of 4 h.

The following examples are illustrative examples in which the decrease in activity and selectivity using different catalysts from those described in the present invention are demonstrated.

Example 16

Use of Catalyst H in the Transposition of β-Pinene Epoxide

Material H was used in the procedure described in example 11 in acetonitrile and it was observed that after 2 h of reaction time, the conversion was less than 5%.

Example 16

Use of Catalyst I in the Transposition of β-Pinene Epoxide

Material I was used in the procedure described in example 11 in acetonitrile and it was observed that after 2 h of reaction time, the conversion was less than 23% and selectivity for myrtanal was 53%.

Example 17

Use of Catalyst J in the Transposition of β-Pinene Epoxide

Material J was used in the process described in example 7 in acetonitrile and it was observed that after 2 h of reaction time, the conversion was less than 5%.

The invention claimed is:

1. A process for the transposition of β-pinene epoxide to myrtanal characterised in that it comprises carrying out a reaction with this epoxide in the presence of a microporous and crystalline catalyst with pores with a diameter of at least 0.52 nm that has an empirical formula in its calcinated and dehydrated form of $H_w(M_wTi_xSn_yZr_zSi_{1-w-x-y-z})O_2$ where M is at least a metal with valence+3 selected from Al, B, Ga, Fe, Cr and combinations of these;

w is a molar fraction of M with a value of between 0 and 2(x+y+z);

x is a molar fraction of titanium and has a value of between 0 and 0.06;

y is a molar fraction of tin and has a value of between 0 and 0.06;

z is a molar fraction of zirconium and has a value of between 0 and 0.06;

and where at least one of the three values "x", "y" or "z" is different from zero.

2. The process according to claim 1 characterised in that the catalyst has pores with a diameter of at least 0.52 nm and with a crystalline structure with an X-ray diffractogram of a zeolite beta.

3. The process according to claim 1 characterised in that in the formula of the catalyst in the calcinated and dehydrated form, "x" has a value of between 0.002 and 0.06, "y" has a value of between 0 and 0.06 and "z" has a value of between 0 and 0.06.

4. The process according to claim 1 characterised in that in the formula of the catalyst in the calcinated and dehydrated form, "y" has a value of between 0.002 and 0.06, "x" has a value of between 0 and 0.06 and "z" has a value of between 0 and 0.06.

5. The process according to claim 1 characterised in that in the formula of the catalyst in the calcinated and dehydrated form, "z" has a value of between 0.002 and 0.006, "x" has a value of between 0 and 0.06 and "y" has a value of between 0 and 0.06.

6. The process according to claim 1 characterised in that it comprises the use of a solvent.

7. The process according to claim 6 characterised in that said solvent is selected from acetonitrile, dioxane, nitromethane, diethyl ether, methyl tert-butyl ether, toluene, methanol, ethanol, isopropanol and mixtures of these.

8. The process according to claim 7 characterised in that said solvent is acetonitrile.

9. The process according to claim 1 characterised in that the epoxide is in a solution from 10% to 90% by weight.

10. The process according to claim 9 characterised in that the epoxide is in a solution from 10% to 50% by weight.

11. The process according to claim 1 characterised in that it is carried out at a temperature of between 20° C. and 150° C.

12. The process according to claim 11 characterised in that it is carried out at a temperature of between 40° C. and 120° C.

13. The process according to claim 1 characterised in that it is carried out in a continuous or discontinuous reactor.

* * * * *